(12) United States Patent
Paulson

(10) Patent No.: US 9,545,327 B2
(45) Date of Patent: Jan. 17, 2017

(54) PRESSURIZED LIQUID CAST

(71) Applicant: Molly J. Paulson, Grand Rapids, MI (US)

(72) Inventor: Molly J. Paulson, Grand Rapids, MI (US)

( * ) Notice: Subject to any disclaimer, the term of this patent is extended or adjusted under 35 U.S.C. 154(b) by 290 days.

(21) Appl. No.: 14/043,173

(22) Filed: Oct. 1, 2013

(65) Prior Publication Data
US 2014/0107550 A1    Apr. 17, 2014

Related U.S. Application Data

(60) Provisional application No. 61/712,554, filed on Oct. 11, 2012.

(51) Int. Cl.
*A61F 5/01*    (2006.01)
*A61F 5/058*   (2006.01)

(52) U.S. Cl.
CPC ............. *A61F 5/012* (2013.01); *A61F 5/0585* (2013.01); *A61F 5/05833* (2013.01); *A61F 5/05858* (2013.01)

(58) Field of Classification Search
CPC combination set(s) only.
See application file for complete search history.

(56) References Cited

U.S. PATENT DOCUMENTS

| | | |
|---|---|---|
| 2,823,668 A | 2/1958 | Van Court et al. |
| 3,186,404 A | 6/1965 | Gardner |
| 3,186,405 A | 6/1965 | Bailey et al. |
| 3,403,676 A | 10/1968 | Gibbons |
| 3,424,151 A | 1/1969 | Ericson |
| 3,561,435 A | 2/1971 | Nicholson |
| 3,643,656 A | 2/1972 | Young et al. |
| 3,701,349 A | 10/1972 | Larson |
| 3,745,998 A | 7/1973 | Rose |

(Continued)

FOREIGN PATENT DOCUMENTS

| | | |
|---|---|---|
| CN | 201930109 | 8/2011 |
| GB | 1171361 | 11/1969 |

(Continued)

OTHER PUBLICATIONS

First Aid Products.com, Inflatable Air Splints, http://www.first-aid-product.com/industrial/inflatable-air-splints.htm, Jul. 27, 2012, 3 pages.

*Primary Examiner* — Ophelia A Hawthorne
(74) *Attorney, Agent, or Firm* — Gardner, Linn, Burkhart & Flory, LLP

(57) ABSTRACT

A pressurized fluid cast for stabilizing a broken bone of a patient includes a sleeve having an inner wall and an outer wall with a fluid cavity between the inner and outer walls. The outer wall has at least one access port established therethrough. The sleeve is configured to be placed at a limb of a patient such that the inner wall circumscribes the limb and is disposed at least partially along the limb, with the fluid cavity and the outer wall being radially outward of the inner wall. The sleeve is adaptable to accommodate a particular patient injury and limb. Fluid is provided within the fluid cavity and is pressurized to a selected pressure to apply substantially uniform pressure at the limb of the patient. An outer protective shell may be provided at least partially around the sleeve to limit puncturing of the sleeve.

19 Claims, 3 Drawing Sheets

(56) References Cited

U.S. PATENT DOCUMENTS

| | | | |
|---|---|---|---|
| 3,786,805 A | 1/1974 | Tourin | |
| 3,955,565 A | 5/1976 | Johnson, Jr. | |
| 4,157,713 A | 6/1979 | Clarey | |
| 4,387,710 A * | 6/1983 | Beatty, III | A61F 13/046 602/14 |
| 4,393,867 A | 7/1983 | Baron | |
| 4,621,624 A | 11/1986 | Rayboy | |
| 4,657,003 A | 4/1987 | Wirtz | |
| 4,817,590 A | 4/1989 | Stancik, Jr. | |
| 5,288,286 A | 2/1994 | Davis et al. | |
| 5,527,293 A * | 6/1996 | Zamierowski | A61F 5/453 128/898 |
| 5,577,998 A | 11/1996 | Johnson, Jr. et al. | |
| 5,718,669 A | 2/1998 | Marble | |
| 5,728,052 A * | 3/1998 | Meehan | A61F 15/004 602/3 |
| 5,954,676 A | 9/1999 | Kramer, III | |
| 6,066,107 A | 5/2000 | Habermeyer | |
| 6,409,691 B1 | 6/2002 | Dakin et al. | |
| 6,478,757 B1 | 11/2002 | Barak | |
| 6,719,711 B1 | 4/2004 | Islava | |
| 7,585,285 B2 | 9/2009 | Pone et al. | |
| 7,828,757 B2 * | 11/2010 | Blocker | A61F 13/046 601/11 |
| 7,896,910 B2 | 3/2011 | Schirrmacher et al. | |
| 7,942,840 B2 | 5/2011 | Hargrave et al. | |
| 8,052,628 B1 | 11/2011 | Edelman et al. | |
| 8,075,506 B2 | 12/2011 | Linares | |
| 8,226,585 B2 | 7/2012 | Pick et al. | |
| 2001/0039439 A1 * | 11/2001 | Elkins | A61F 7/10 607/104 |
| 2006/0173390 A1 | 8/2006 | Van Wyk et al. | |
| 2008/0183115 A1 * | 7/2008 | Pierce | 602/13 |
| 2010/0160843 A1 | 6/2010 | Neely | |
| 2011/0306910 A1 | 12/2011 | Siegner | |

FOREIGN PATENT DOCUMENTS

| | | | |
|---|---|---|---|
| GB | 2416491 | 2/2006 | |
| GB | 2416491 A * | 2/2006 | A61F 13/04 |
| WO | WO2011082176 | 7/2011 | |

\* cited by examiner

PRESSURIZED LIQUID CAST

The present application is related to U.S. provisional application, Ser. No. 61/712,554, filed Oct. 11, 2012, which is hereby incorporated herein by reference in its entirety.

FIELD OF THE INVENTION

The present invention relates generally to casts for immobilizing broken bones or other types of injuries.

BACKGROUND OF THE INVENTION

Currently casts for immobilizing or stabilizing a patient's injury are made using either plaster or fiberglass (where the material is molded over the patient's arm or leg or the like to immobilize the injury) or are premade in generic variable adjustable sizes. The fit of a plaster and/or fiberglass cast is dependent on the skill of the medical provider and even a skilled provider may not be able to fit a cast perfectly as soft tissue swelling may be variable during the time of healing. The variability in fit decreases the comfort during the healing process and can delay the healing process and/or may cause iatrogenic infection or other soft tissue damage, such as compartment syndrome or the like, if the cast is too tight and cuts off circulation to a distal extremity. Changes in swelling, comfort issues or other concerns may require that a second cast or even a third cast be placed or the placement of the cast may be delayed to allow for soft tissue swelling to go down.

These issues increase medical costs to the patient and insurance company due to increased provider time with the patient. In addition, there is an increased cost to society due to delay in return to work due to pain, disability, increased office or procedure visits and increased length of healing time. While some adjustable casts have been proposed that may be adjusted to adapt to changes in swelling, such proposed casts do not provide enough stability for many types of fractures.

SUMMARY OF THE INVENTION

The present invention provides an adjustable cast that utilizes pressurized liquid to provide sufficient stabilization and immobilization of a patient's injury, while allowing for the cast to adapt and conform to the patient when changes in swelling and the like occur. The present invention thus stabilizes a fracture using fluid pressure or hydrostatic pressure, such that the fit of the cast is always perfect and adapts to changes in soft tissue swelling. Because the cast contains pressurized fluid, the fluid can be cooled to decrease pain and swelling or heated to increase circulation around the injured area.

The cast of the present invention provides a low-pressure system where the fluid pressure can be adjusted continuously (such as via a circulating pump with attached pressure monitor) or intermittently based on the individual patient's fracture needs. The cast may be immersed in water for bathing without damage to the cast or fracture. The casting material and equipment of the present invention is portable and can be brought to site of trauma and applied onsite to stabilize the injury before transport of the patient, thereby limiting or preventing further injury, and the cast can be quickly and easily removed later if surgery is required. If a fluid pressure cast of the present invention is placed to protect a fracture or control bleeding at trauma site, it can be easily removed such as cut off with a scissors or the like instead of a cast saw which fills the air (and possibly trauma wounds) with dust. The cast of the present invention can be sterilized prior to placement in surgery to cut down on the risk infection if an open reduction of a fracture is required. The cast of the present invention may be readily removed and/or formed with apertures or holes therethrough, such that the areas where pins are placed may be visualized and inspected for infection as needed.

Therefore, the fluid pressure cast of the present invention may be quickly and/or easily and/or readily placed on a patient and is less dependent (or not dependent at all) on provider skill, and requires less provider time to fit the cast. The materials of the cast of the present invention are inexpensive and lightweight. Because the cast of the present invention is adjustable, the cast can be placed on the same day as the occurrence of the fracture without concern of swelling or compartment syndrome, thereby resulting in reduced amount of repeat visits to the provider for refitting. Because the cast of the present invention can always be adjusted to provide a perfect or nearly perfect fit, the patient experiences greater comfort and support of the injury. The patient may also experience a decreased need for pain medication as the cast can be cooled constantly or intermittently as needed for comfort. Thus, the present invention provides for improved patient satisfaction and decreased medical costs.

These and other objects, advantages, purposes and features of the present invention will become more apparent upon review of the following specification in conjunction with the drawings.

DESCRIPTION OF THE PREFERRED EMBODIMENTS

Figure 1:
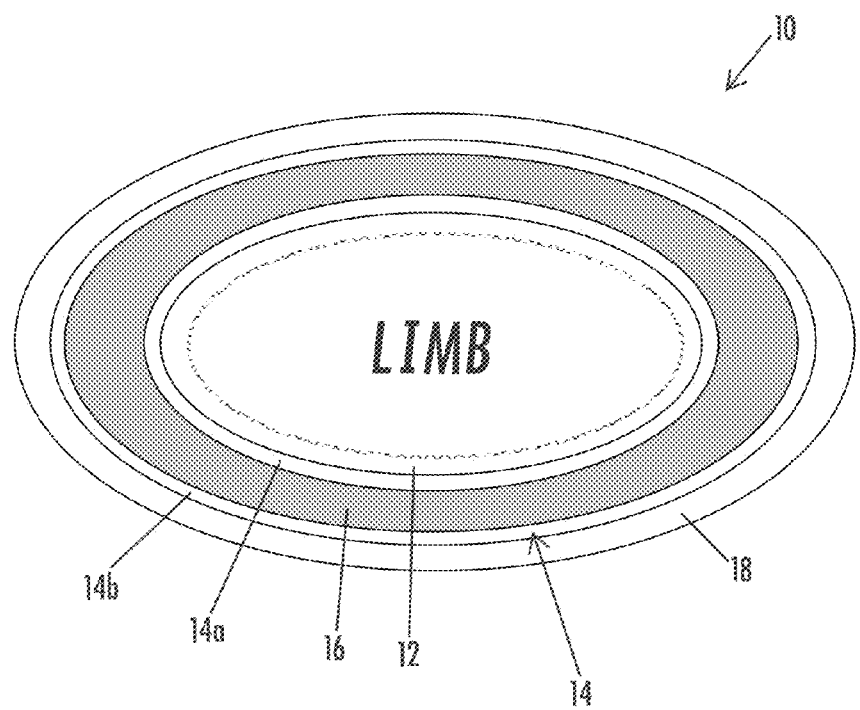
FIG. 1 is a cross sectional view of a pressurized liquid cast in accordance with the present invention.

Referring now to the drawings and the illustrative embodiments depicted therein, a fluid pressure cast 10 is inflatable/deflatable/adjustable to conform to a patient's injured area to stabilize and/or immobilize the injury during the healing process (such as after a broken bone is set). The cast 10 includes an inner layer 12 (such as a fabric layer or wicking layer that functions to absorb sweat and to reduce friction and rubbing at the patient's skin), a pressurized sleeve 14 that contains a pressurized fluid 16 therein and has an inner waterproof layer or wall 14a and an outer waterproof layer or wall 14b. An outer protective layer or shell 18 may be disposed over the outer wall 14b of the sleeve 14 to protect the fluid pressurized cast 10. The cast 10 thus provides an adjustable cast where adjusting the pressure of the fluid 16 in the sleeve 14 increases or decreases the pressure at the injury and allows the cast to conform to the injured patient and maintain a desired pressure at the injury regardless of any increase or decrease in swelling at or near the injury, as discussed below.

The innermost circular layer 12 may comprise any suitable material, such as a stretchable wicking fabric such as used in athletic clothes to protect the skin and provide for ease in placing the deflated cast. The inner wall 14a of the sleeve or tube 14 may comprise a latex/plastic waterproof circular inner layer that stretches or shrinks to conform to the human body in a pressure-dependent manner, while the outer wall 14b of the sleeve or tube 14 may comprise a latex/plastic waterproof circular outer layer that adjusts in a pressure-dependent manner to the volume of the fluid or fluid layer 16 within the sleeve or tube 14. As can be seen with reference to FIG. 1, the sleeve comprises a continuous sleeve and cavity around the patient's limb, such that inner wall 14a of the sleeve circumscribes the patient's limb and extends at least partially along the patient's limb, such that, when the sleeve is pressurized, the inner wall 14a conforms to the patient's limb and applies a substantially uniform pressure at and around and along the patient's limb to stabilize the limb during the healing process. Optionally, the outer wall 14b may include stabilizing ribs and/or baffles to further stabilize the fracture and/or to provide a pressure gradient to improve circulation and decrease the risk of blood clots in the patient.

The outer layer or shell 18 is an adjustable protective shell to protect the sleeve of the cast from punctures or other damage. Optionally, for example, the outer layer 18 may be made of canvas (in various or selected colors if desired) or a combination of plastics with rigid or semi-rigid (plastic or metal) ribs to further support and stabilize the fracture. Optionally, the outer layer may comprise a semi-rigid or hard durable plastic material, whereby the outer layer may be adjustably disposed at and fit over the sleeve and the patient's injury. For example, the outer layer may comprise a clamshell type design with two or more semi-rigid portions hingedly joined together and adjustable to accommodate the patient's arm or leg or the like. Optionally, the two or more portions may be secured via a ratcheting type connection to set the desired diameter of the outer layer or via hook and loop type fasteners (such as VELCRO® strips or the like) to set the desired size and tension at the outer layer.

The fluid or fluid layer in the sleeve may comprise any suitable fluid, and may be selected or determined by what the physician feels is the most appropriate for the individual fracture. For example, if there is a lot of soft-tissue swelling at the targeted patient injury that will benefit from cooling, a combination of water and alcohol may be used as the fluid to maintain cooling over a period of several hours. There are several options available, both liquid and gel and the like, that may be appropriate to use to stabilize the fracture and maintain the preferred temperature to optimize comfort and healing.

The cast of the present invention may be provided as a premade cast that may be commercially provided in various sizes and for various applications. For example, adjustable casts of the present invention may be provided as small, medium and large ankle casts, small, medium and large full leg casts, small medium and large arm casts and/or the like. Thus, a medical provider may select an appropriate cast depending on the patient size and type of injury and may readily apply the selected cast to the patient.

Figure 5:
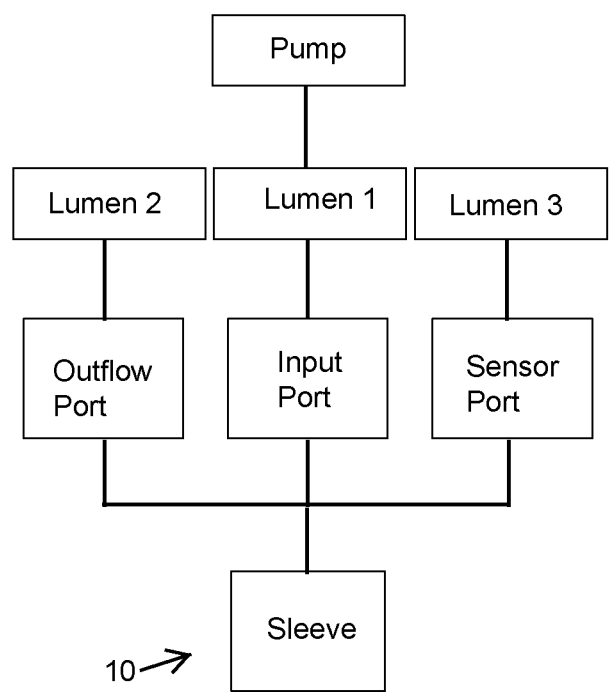
FIG. 5 is a schematic diagram of the pressurized liquid cast and other components in accordance with the present invention.

Such premade casts may be sized and shaped for the various applications at upper and lower extremities. The premade cast comprises a premade or pre-sized sleeve (that contains fluid or that is configured to contain fluid within a fluid cavity that circumscribes and defines a passageway along the cast or sleeve. The cast includes one or more access ports 20 in the outer layer or shell, and has a lumen attachment or connector for connecting to a fluid pump or supply source. Optionally, the attachment may comprise a triple lumen attachment for (a) input of fluid (heated or cooled), (b) a pressure gauge or sensor, and (c) outflow of excess fluid (to reduce pressure), such as shown in FIG. 5. Thus, the fluid may be circulated through the fluid cavity of the sleeve to provide the desired or selected or appropriate pressure and to provide temperature adjustment (via circulating warmer or cooler fluid through the fluid cavity) of the fluid within the sleeve.

The pressure may be increased by adding fluid through the inlet port while the outlet port is closed and the pressure may be decreased by allowing fluid to flow through the outlet port while not adding fluid through the inlet port. The flow of fluids may be automatic in response to the pressure sensor (to maintain a selected pressure of fluid in the cavity) or may be manually increased or decreased by the patient or medical provider. By providing a system that maintains a generally constant pressure at the injury and generally uniformly around the injured limb or extremity, the cast provides generally constant pressure at the injury even if swelling increases or decreases, without having to adjust or remove or replace the cast. The cast is very useful for simple fractures that are not expected to swell a great deal and primarily needed for stabilization and comfort while the fracture heals.

Also, it is envisioned that the premade cast may be useful in the field for trauma. For example, if a patient is found with multiple fractures, lacerations and urgent injuries that require a lot of medical attention, the premade cast may be placed quickly (as quickly as a sock) on the less urgent fracture to stabilize the injury (and prevent further injury) so that full attention may be given to the more urgent injuries. In addition, the premade cast may be used to control the bleeding of arteries and veins by applying the cast over the area of bleeding and establishing a pressure at the bleed area that is sufficient to limit or stop the bleeding, while keeping the area clean and not causing ischemic damage below the cast. The premade cast of the present invention may be a lifesaver in a war zone as it is lightweight to carry, adjustable and reusable. Optionally, shorter casts (comprising a sleeve as described above with a length of about six inches or more or less) may be made in accordance with the present invention for application to cuts and the like to control the bleeding of such injuries.

Figure 2:
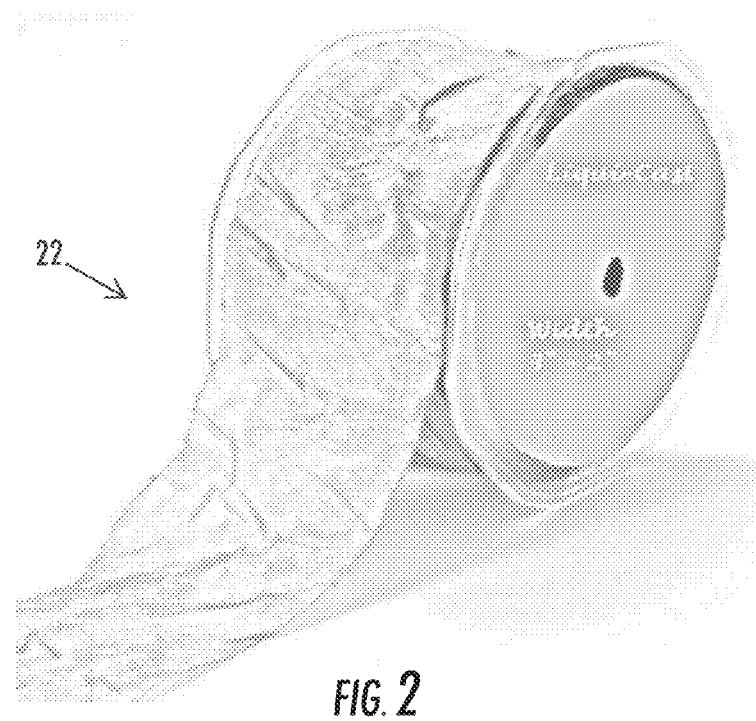
FIG. 2 is a perspective view of a roll of sleeve or tubing material for forming a customized pressurized liquid cast in accordance with the present invention.
Figure 3:
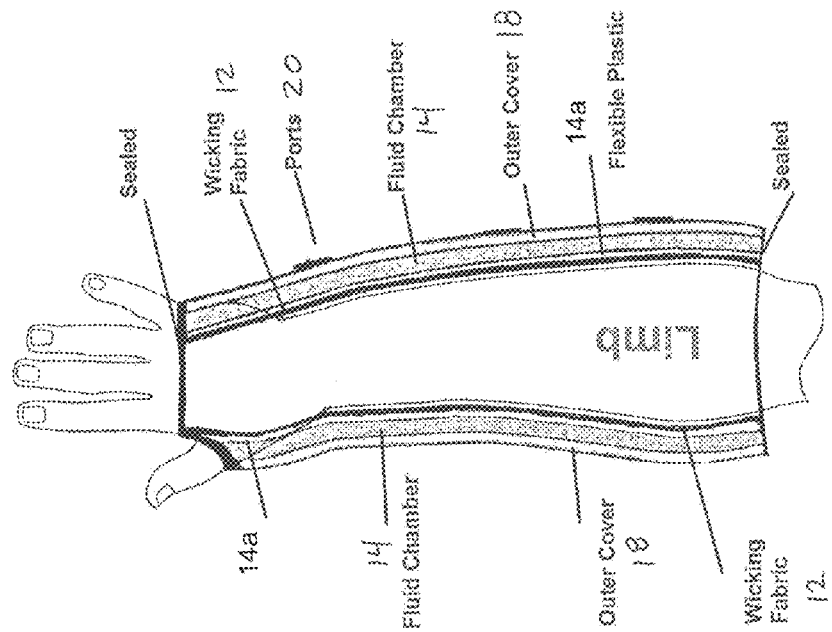
FIG. 3 is a perspective view of a preformed or completed customized pressurized liquid cast of the present invention, as applied at a patient's arm.
Figure 4:
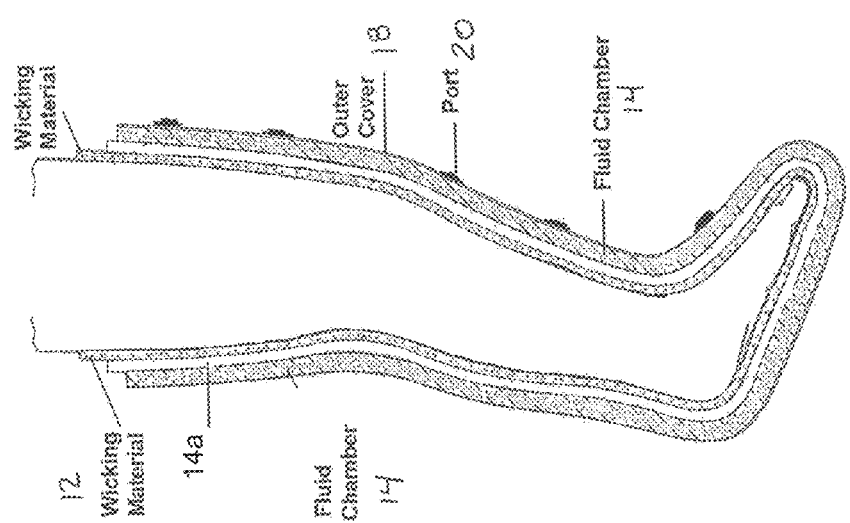
FIG. 4 is a perspective view of a pressurized liquid cast of the present invention, as applied at a patient's leg.

Optionally, the cast of the present invention may be provided as a customizable cast, where the materials are provided as a kit and a medical provider forms the cast specifically for a particular patient and injury. For example, custom cast kits may be provided as double rolls (in different widths) of the sleeve or tube in a box similar to what is used currently for stockinet. The rolls 22 (FIG. 2) can be customized to the individual patient using a sealer machine (such as a heat sealing type device or the like). For example, the medical provider (such as the medical doctor, physician assistant, nurse practitioner or medical assistant or trained or registered nurse or the like) unwinds the appropriate width roll of tubing from the storage box, and measures and cuts the appropriate length to be used. The provider then determines how many access ports are needed in the outer layer or wall of the sleeve or tube and, using the sealing device (such as a heat sealing device that may melt apertures or the like through the sleeve wall and/or may melt and seal the walls of the sleeve together) makes the port accesses. If finger or toe holes are needed, these are done thru both layers of the tube or sleeve. If a joint needs to be held at an angle, darts can be sealed into the layers of the tube or sleeve so that the sleeve takes on the desired bend or curvature for the particular application.

When the sleeve is adjusted and formed to the desired configuration, the ends of the sleeve may be sealed (by sealing the inner and outer sleeve walls or layers at the ends of the sleeve to provide or form an opening at each end of the sleeve). The cast is then placed over the injured extremity (such as by first placing the fabric layer over the injury and then sliding the formed sleeve into place over the injury) and a small fluid pump is attached and pressure is set. Then, with actuation of a user input, such as a simple push of a button, fluid is pumped into the cast. Any air bubbles that may form may be released from a vent or upper port. In the field, any available and suitable fluid or liquid may be injected into the sleeve of the cast using a syringe or small manual or electronic pump to obtain the appropriate pressure.

The custom cast kit or system thus includes a sealing device, such as a known sealing device that is similar to what is used to seal two layers of plastic together. The sealing device is used to seal the ends of the cast at custom lengths as decided by the medical provider. The sealing device will also have the ability to form thumbholes or openings thru the walls of the tube of the cast for the patient's thumb or finger and/or for pins or other hardware as may be required by the provider. For example, the sealing device may form a hole through both walls of a portion of the sleeve and seal the inner and outer walls together around the hole or aperture to form a hole through the sleeve, whereby pressurized fluid may flow into the sleeve and around the hole, with little or no leakage of fluid at the hole. The sealing device may also be used to form darts or bends in the tube or sleeve of the cast to optimize the correct anatomic positioning of the cast at the patient. Optionally, variable sizes of these custom casts may be premade in a forming facility for additional ease of use in the field.

The custom cast kit or system also includes an access port catheter. Catheter ports may either be manufactured into the outer layer or may be custom made using the sealing device. Once placement of the catheter is determined by the medical provider (or cast manufacturer), a catheter, which may be a multi-lumen catheter (such as a triple lumen catheter or double lumen catheter or the like), may be placed thru the outer layer into the potential space or cavity of the sleeve without disturbing the integrity of the inner layer. This provides the means to place liquid into the sealed sleeve cavity. The catheter may remain open to allow constant movement of fluid in and out of the cast thereby maintaining generally constant temperature and pressure or it can be closed off (after the fluid is set to the desired pressure within the cavity) to allow freedom of movement of the patient's limb and the patient.

A pressure gauge or pressure sensor may be used to set and monitor the appropriate amount of pressure to stabilize the fracture or to control bleeding. The pressure gauge may be in communication with the pressurized fluid in the cavity of the sleeve to determine and indicate the fluid pressure in the cavity.

A temperature and pressure modulating pump is used to pump and circulate fluids in a controlled manner into the sleeve cavity (between the circular inner and outer layers or walls of the sleeve). This pump also has the ability to maintain a provider-specified temperature and pressure within the cast. The pump can be detached and reattached (at one of the lumens of the access port catheter) as needed to satisfy the recommendations of the medical provider. For example, the pump may be connected at one of the lumens of the catheter, while the pressure gauge may be connected at another of the lumens, or the pump may include a pressure determining function and may be operable to modulate the fluid to be at a selected pressure or within a threshold amount of a selected pressure (such that no separate pressure sensor is needed).

Thus, when a custom cast is made in the field, a medical provider first measures the affected or injured extremity to determine the appropriate cast length and width. The medical provider may roll out the appropriately sized sleeve and cut it to appropriate length. The medical provider may then determine the appropriate location or placement of the access port opening or openings and/or finger holes or openings and/or any hardware holes or openings and then may use the sealing device to establish and seal any such desired or necessary access ports and necessary openings. If needed or desired, the medical provider may also (such as by using the sealing device) make any appropriate darts or creases or bends in the sleeve walls to obtain an enhanced or optimal anatomic positioning of the cast to enhance the healing process. The medical provider (using the sealing device) may seal the ends of the sleeve walls together to close and seal the cavity of the sleeve. The finished sleeve may be slid over the affected or injured extremity and positioned appropriately at the injury, whereby fluid may be added to the cavity of the sleeve and pressurized to the desired or appropriate pressure. For example, the medical provider may attach the pump to the access port and may set the pressure and temperature to appropriate levels, and then may turn on the pump to inject the fluid into the cast. The pump will automatically stop when the appropriate pressure is reached. Once the sleeve is pressurized to the desired pressure, an outer protective shell may be used to cover and encase the sleeve to protect the sleeve against puncturing and the like. After the sleeve is pressurized to the desired pressure, the pump may be detached as needed for mobility or transport of the patient.

Thus, the present invention provides a flexible cast for a fracture that stabilizes the bone with the addition of temperature therapy to decrease swelling and provide pain relief and comfort. For example, cooler fluid may be initially provided to slow or reduce initial swelling at the injury site and later warmer fluid may be provided to increase blood flow to the injured area to enhance healing. The "cast", instead of being made of fiberglass or plaster, uses pressurized fluid to provide hydrostatic stability. The fluid is contained in a fabric covered expandable plastic tube. A benefit of using pressurized fluid is that the "fluid cast" will fit each individual injury perfectly, without seams, and the fluid cast is much less dependent on the medical provider's skill at forming the cast. This will prevent superficial rubbing, irritation and actually will provide better fracture stability because the pressure will be symmetrical on the surrounding tissue. Because the plastic sleeve or tube is susceptible to damage, a durable hard plastic cover or splint (that is preferably adjustable) is preferably placed over the "fluid cast" to provide additional stability and limit or substantially preclude perforation of the fluid filled tube or sleeve. Another benefit of the fluid cast is that it is water resistant and thus may be gotten wet so showers and cleaning of the patient is made easier by the cast of the present invention.

For example, when a limb (such as an arm or leg) is broken, if the broken bones are out of alignment, the bones must be "reduced" or placed in alignment or set (typically requiring two medically trained personnel) in order to heal in a functional position, and the bones may be unstable and hard to heal if not held in alignment for a prolonged period of time. Once the bones are in place, if a conventional cast is to be applied, the orthopedic providers (typically two are required) work in tandem to wrap the forearm in plaster or fiberglass while attempting to hold the bones in place with traction. They continue to maintain the traction at the injury until the cast hardens. Next, they x-ray the injury to confirm the proper alignment of the bones and may have to redo the whole procedure if the bones slipped while they are wrapping the arm (and if they have to re-cast the limb, they first they have to take off the cast they just put on). Because of the trauma to the tissues as well as the bones and because of all the pulling and twisting that the providers do to get the bones back in place-the soft tissues typically swell in the hard inflexible cast, sometimes cutting off circulation in the limb. This causes severe pain and can cause permanent damage to tissues at the area of swelling and below. If it is bad enough, the providers have to do the whole procedure again (stabilize the bone and make a new larger cast). Then, when the swelling goes down, the pressure at the injury is reduced and the bone is no longer stabilized and can move. The procedure can start all over again or surgery may be needed to fix the bones.

The present invention alleviates many of the above concerns with conventional plaster cast approaches. With the cast of the present invention, once the broken bones are set or aligned, the limb is encased in a tube that is slightly flexible/adjustable (and optionally, the tube can be customized by heating to fuse the plastic together). The provider aligns the bones or makes sure they are in alignment, and then, instead of having to wrap a plaster cast around the broken limb, the provider simply fill the cast with fluid to the appropriate pressure to stabilize the bone or limb or extremity. Such a procedure may be performed by a single medical provider. After the fluid cast is pressurized, an x-ray may be taken to make sure the bones are in alignment and then the fluid supply and/or pressure may be adjusted to maintain a generally constant pressure at the limb as swelling may increase or decrease. If the bones are not properly aligned, the cast may be slightly drained, and the provider may realign the bones, and then re-fill the cast and repeat the x-ray. There is no need to take the cast off, and no need to move the limb while wrapping material around the limb. The limb just needs to be held still in traction until the sleeve is positioned at the limb and pressurized.

The present invention thus provides a casting process that is much less traumatic for both the patient and the provider. The casting process of the present invention also provides a faster process since the provider only has to fill the fluid cast that may already be in place before the bones are aligned. If there is swelling, the compressor adjusts the pressure of the cast to maintain fracture stability, and allow good blood flow and prevent tissue damage, all without having to remove and replace the cast. When the swelling goes down, the reverse occurs and fluid may be added to the cast to maintain the desired pressure at the injured limb. The cast of the present invention thus provides substantially uniform or symmetrical pressure around and along the patient's limb or extremity, even as the patient may experience an increase or decrease in swelling at the injury site. The hard outer shell protects the cast from damage. The benefit of the fluid cast is that the provider or the patient can also use the fluid via a pump as a way to do temperature therapy on the soft tissue while stabilizing the break to enhance healing of the injured limb.

Changes and modifications to the specifically described embodiments may be carried out without departing from the principles of the present invention, which is intended to be limited only by the scope of the appended claims as interpreted according to the principles of patent law including the doctrine of equivalents.

The embodiments of the invention in which an exclusive property is claimed are defined as follows:

1. A method of applying a pressurized fluid cast at a limb of a patient, said method comprising:
    providing a sleeve having an inner wall and an outer wall with a cavity between said inner and outer walls;
    wherein providing a sleeve comprises (i) cutting an appropriate length sleeve from a roll of tubing material to form a sleeve for a particular limb and (ii) sealing said inner and outer walls together at the ends of the cut sleeve;
    providing at least one access port through said outer wall of said sleeve;
    placing said sleeve at a limb of a patient such that said inner wall circumscribes the limb and is disposed at least partially along the limb, with said cavity and said outer wall being radially outward of said inner wall;
    providing fluid to said cavity of said sleeve and pressurizing said fluid to a selected pressure to apply substantially uniform pressure at the limb of the patient; and
    adjusting the pressure of said fluid within said cavity responsive to a determined change in pressure indicative of a change in swelling of the limb of the patient.

2. The method of claim 1, wherein pressurizing said fluid comprises pressurizing said fluid via a fluid pump in communication with said at least one access port.

3. The method of claim 2, further comprising sensing flow of said fluid via a pressure sensor within said cavity of said sleeve, wherein said fluid pump is responsive to pump said fluid.

4. The method of claim 2, wherein said fluid pump is selectively operable to increase or decrease the amount of fluid within said cavity of said sleeve.

5. The method of claim 2, comprising closing said access port and disconnecting said fluid pump when a desired pressure is achieved.

6. The method of claim 1, wherein cutting said appropriate length sleeve and sealing said inner and outer walls together at the ends of the cut sleeve are done at the patient to provide a custom sleeve for the particular limb of the particular patient.

7. The method of claim 1, further comprising shaping said sleeve to a desired shape so said sleeve generally conforms to the shape of the particular limb at which it is placed.

8. The method of claim 1, comprising forming an aperture through said inner wall and said outer wall and sealing together said inner and outer walls around said aperture so that said aperture provides a passageway through said sleeve.

9. The method of claim 1, comprising providing an inner wicking layer around and at least partially along the limb before placing said sleeve at the limb.

10. The method of claim 1, comprising providing an outer protective layer around said outer layer of said sleeve, wherein said outer protective layer is formed of a semi-rigid or rigid material that limits puncturing of said outer wall.

11. The method of claim 1, comprising adjusting a temperature of fluid within said fluid cavity.

12. A pressurized fluid cast for stabilizing a broken bone of a patient, said pressurized fluid cast comprising:

a sleeve having an inner wall and an outer wall with a fluid cavity between said inner and outer walls;

wherein said outer wall has at least one access port established therethrough;

wherein said sleeve is configured to be placed at a limb of a patient such that said inner wall circumscribes the limb and is disposed at least partially along the limb, with said fluid cavity and said outer wall being radially outward of said inner wall;

wherein said sleeve is adaptable to accommodate a particular patient injury and limb;

wherein fluid is provided within said fluid cavity and is pressurized to a selected pressure to apply substantially uniform pressure at the limb of the patient; and a multi-lumen catheter at said at least one access port, wherein a first lumen of said multi-lumen catheter is connected to a fluid pump for supplying fluid to said fluid cavity and wherein a second lumen of said multi-lumen catheter is configured to drain fluid from said fluid cavity.

13. The pressurized fluid cast of claim 12, wherein said fluid is pressurized via said fluid pump in communication with said first lumen at said at least one access port.

14. The pressurized fluid cast of claim 13, further comprising a pressure sensor that senses flow of said fluid within said fluid cavity of said sleeve, wherein said fluid pump is responsive to said pressure sensor.

15. The pressurized fluid cast of claim 12, comprising an inner wicking layer disposed around and at least partially along the limb and radially inward of said inner wall.

16. The pressurized fluid cast of claim 12, comprising an outer protective layer radially outward of said outer wall, wherein said outer protective layer is formed of a semi-rigid or rigid material that limits puncturing of said outer wall.

17. The pressurized fluid cast of claim 12, wherein a temperature of fluid within said fluid cavity is adjustable.

18. The pressurized fluid cast of claim 12, wherein an aperture is formed through said inner wall and said outer wall and wherein said inner and outer walls are sealed together around said aperture so that said aperture provides a passageway through said sleeve.

19. The pressurized fluid cast of claim 12, wherein fluid is provided within or removed from said fluid cavity to maintain the selected pressure as swelling of the limb of the patient decreases or increases.

* * * * *